(12) United States Patent
Royce et al.

(10) Patent No.: US 9,181,583 B2
(45) Date of Patent: Nov. 10, 2015

(54) HLA TYPING USING SELECTIVE AMPLIFICATION AND SEQUENCING

(71) Applicant: Illumina, Inc., San Diego, CA (US)

(72) Inventors: Thomas Royce, San Diego, CA (US); Craig April, La Jolla, CA (US); Fiona Kaper, Encinitas, CA (US); Jian-Bing Fan, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 447 days.

(21) Appl. No.: 13/790,112

(22) Filed: Mar. 8, 2013

(65) Prior Publication Data

US 2014/0114579 A1    Apr. 24, 2014

Related U.S. Application Data

(60) Provisional application No. 61/717,495, filed on Oct. 23, 2012.

(51) Int. Cl.
*C12Q 1/68* (2006.01)
*G06F 19/16* (2011.01)

(52) U.S. Cl.
CPC ............ *C12Q 1/6874* (2013.01); *C12Q 1/6827* (2013.01); *C12Q 1/6853* (2013.01); *C12Q 1/6883* (2013.01); *G06F 19/16* (2013.01); *C12Q 2600/172* (2013.01)

(58) Field of Classification Search
None
See application file for complete search history.

(56) References Cited

U.S. PATENT DOCUMENTS

2010/0086914 A1    4/2010    Bentley et al.
2010/0261189 A1*  10/2010   Bentley ............... C12Q 1/6869
                                             435/6.11

FOREIGN PATENT DOCUMENTS

| WO | 98/35059 | 8/1998 |
|---|---|---|
| WO | 02/097047 | 12/2002 |
| WO | 2005/017652 | 2/2005 |

OTHER PUBLICATIONS

Beckmann, et al., "Resolution of Haplotypes and Haplotype Frequencies from SNP Genotypes of Pooled Samples", ACM, 2 Penn Plaza, Suite 781—New York USA, vol. RECOMB, XP848145659, Apr. 13, 2003, 237-245.

Bentley, et al., "High-Resolution, High-Throughput HLA genotyping by next-generation sequencing," Tissue Antigens, vol. 74, No. 5, XP055087325; ISSN: 0001-2815, DOI: 10.1111/j.1399-0039.2009.01345.x, Nov. 1, 2009, 393-403.

Fuernkranz, et al., "Top-Down Pruning in Relational Learning", Proceedings European Conference on Artificial Intelligence, Chichester, GB, XP855889263, Retrieved from the Internet: URL:http://www.plosone.orgjarticle/fetchObject.action?uri=info:doi/18.1371/journal.pone.8867885&representation=PDF [retrieved on Nov. 28, 2813], Aug. 8, 1994, 453-457.

Hosomichi, "Phase-defined complete sequencing of the HLA genes by next-generation sequencing", BMC Genomics, Biomed Central Ltd, London, UK, vol. 14, No. 1, XP021151977, ISSN: 1471-2164, DOI: 10.1186/1471-2164-14-355, May 28, 2013, 335.

Hyunsung, et al., "Haplotyping from RNA-seq Data Using Hierarchical Read Weighting", PLOS one, XP855889263, Retrieved from the Internet: URL:http://www.plosone.orgjarticle/fetchObject.action?uri=info:doi/18.1371/journal.p    one.8867885&representation=PDF [retrieved on Nov. 28, 2813], Jun. 28, 2013.

Liu, et al., "High Resolution HLA Typing by Next Generation Exome Sequencing", 4166—ASH Annual Meeting Abstracts, blood, Retrieved from the Internet: URL:http://abstracts.hematologylibrary.orgjcgijcontentjabstract/120/21/4166?maxtoshow=&hits=10&RESULTFORMAT=&fulltext=high+res olution+hla&searchid=1&FIRSTINDEX=O&volume=120&issue=21&resourcetype=HWCIT [retrieved on Nov. 2013, Nov. 1, 2012, 120 (21).

* cited by examiner

*Primary Examiner* — Jason Sims
(74) *Attorney, Agent, or Firm* — Brent C. Moore; Illumina, Inc.

(57) ABSTRACT

Presented herein are methods and compositions for determining haplotypes in a sample. The methods are useful for obtaining sequence information regarding, for example, HLA type and haplotype. Also presented herein are methods of determining haplotypes in a sample based on a plurality sequence reads.

14 Claims, 4 Drawing Sheets

HLA TYPING USING SELECTIVE AMPLIFICATION AND SEQUENCING

RELATED APPLICATIONS

This application claims priority to U.S. Provisional Application No. 61/717,495, filed on Oct. 23, 2012, which is hereby incorporated by reference in its entirety.

STATEMENT REGARDING FEDERALLY SPONSORED RESEARCH

This invention was made with Government support under NIH Grant AI090905 awarded by the PHS. The Government has certain rights in the invention.

BACKGROUND

Human leukocyte antigen (HLA) genes are critical to humans' adaptive immune response. Because of this, correctly matching the genotypes of these genes between donor and recipient is critical for success in organ transplantation. The most routinely typed HLA genes are HLA-A, HLA-B, HLA-C and HLA-DRB1. HLA sequencing technologies have traditionally focused on the most polymorphic regions encoding the peptide-binding groove that binds to HLA antigens, i.e., exons 2 and 3 for class I genes and exon 2 for class II genes. The antigen-binding groove region of HLA molecules is the focus point of the T-cell receptor and mediates transplant rejection and graft-versus-host diseases (GVHD). For HLA-A, HLA-B and HLA-C, exons 2 and 3 are the most polymorphic exons in the human genome, and are the focus of HLA typing products.

Current DNA-based technologies independently type exons 2 and 3 for HLA-A, HLA-B and HLA-C. This is usually done by DNA hybridization. To gain direct information on the formed proteins, testing can also be done serologically. An alternative method to these is typing by sequencing (sequencing based typing, or SBT). SBT has the potential to provide higher information content than serological or hybridization methods that can, in turn, provide prognostic and diagnostic advantages by avoiding typing ambiguities that plague other methods. However, existing sequencing technologies typically do not have read lengths that allow for complete sequencing of both exons together and/or require cloning each haplotype separately prior to sequencing to resolve within-exonic phase. Also, high error rates are associated with many sequencing technologies. As such, there remains a great need for improved HLA haplotyping methodologies.

BRIEF SUMMARY

Presented herein are methods and compositions for determining haplotypes in a sample. The methods are useful for obtaining sequence information regarding, for example, HLA type and haplotype. In some embodiments presented herein, the methods comprise selectively amplifying nucleic acid molecules, and subsequently sequencing at least a portion of the amplified molecules. The identity of the amplified nucleic acid molecules is then determined based on the sequencing information.

Also presented herein are methods of determining haplotypes in a sample based on a plurality sequence reads. Because sequencing data can be increasingly error-prone with longer read lengths, haplotype information may be difficult to sort out. The methods presented herein advantageously achieve accurate haplotype assignments by using redundant sequencing reads, thus overcoming the high error rates found in existing sequencing-based approaches. Additionally, the clustering methods presented herein also achieve efficient sorting of haplotypes from large sets of low-accuracy sequencing reads.

Accordingly, one embodiment presented herein is a method of determining HLA type comprising: a) selectively amplifying a nucleic acid molecule from an individual, the nucleic acid molecule comprising (i) at least a portion of a first exon of an HLA gene; (ii) at least a portion of a second exon of the HLA gene; and (iii) the intron between the first and second exons, thereby generating an amplified exon pair; b) carrying out a sequencing read of a first region of the amplified exon pair, the first region comprising at least a portion of the first exon and a portion of the intron adjacent to the first exon; c) carrying out a sequencing read of a second region of the amplified exon pair, the second region comprising at least a portion of the second exon and a portion of the intron adjacent to the second exon; and d) determining the HLA type of the individual based on the sequencing reads.

Also presented herein is a method of determining haplotypes in a sample comprising computer implemented steps of providing a computer readable memory comprising sequence information from a plurality of sequencing reads of a region of interest, the plurality of sequencing reads comprising sequence information from at least two different haplotypes; and partitioning each sequencing read into one of two different haplotypes, thereby determining haplotypes in the sample. The partitioning can comprise, for example, application of a k-means-like clustering algorithm or an expectation-maximization clustering algorithm.

In certain embodiments, partitioning comprises computer implemented steps of: (a) randomly selecting a first and second sequencing read from a computer readable memory and designating the reads as haplotype 1 and haplotype 2, respectively; (b) assigning each sequencing read in the plurality of sequencing reads to the haplotype 1 or the haplotype 2 based on sequence similarity to either haplotype 1 or haplotype 2; and (c) computing a consensus sequence for haplotype 1 and a consensus sequence for haplotype 2 using the sequence reads assigned to each haplotype. In certain embodiments, the method further comprises (d) designating the consensus sequences as haplotypes 1 and 2 and repeating steps (b)-(c) until the consensus sequences no longer change.

Also presented herein is a system for determining haplotypes in a sample, the system comprising: a processor; a storage capacity; and a program for determining haplotypes in a sample, the program comprising instructions for: providing sequence information from a plurality of sequencing reads of a region of interest, the plurality of sequencing reads comprising sequence information from at least two different haplotypes; and partitioning each sequencing read into one of two different haplotypes, thereby determining haplotypes in the sample.

Also presented herein is a method of determining HLA haplotype comprising: (a) selectively amplifying a nucleic acid molecule from an individual, the nucleic acid molecule comprising (i) at least a portion of a first exon of an HLA gene; (ii) at least a portion of a second exon of the HLA gene; and (iii) the intron between the first and second exons, thereby generating an amplified exon pair; (b) carrying out a sequencing read of a first region of the amplified exon pair, the first region comprising at least a portion of the first exon and a portion of the intron adjacent to the first exon; (c) carrying out a sequencing read of a second region of the amplified exon pair, the second region comprising at least a portion of the second exon and a portion of the intron adjacent to the second exon; (d) repeating steps (b) and (c) to generate a plurality of paired sequencing reads of the HLA gene, the plurality of paired sequencing reads comprising sequence information from at least two different haplotypes; (e) partitioning each paired sequencing read into one of two different haplotypes, thereby determining haplotypes in the sample; (f) randomly selecting a first and second paired sequencing read and designating the reads as haplotype 1 and haplotype 2, respectively; (g) assigning each paired sequencing read in the plurality of paired sequencing reads to the haplotype 1 or the haplotype 2 based on sequence similarity to either haplotype 1 or haplotype 2; and (h) computing a consensus sequence for haplotype 1 and a consensus sequence for haplotype 2 using the paired sequence reads assigned to each haplotype. In certain embodiments, the method can further comprise (i) designating the consensus sequences as haplotypes 1 and 2 and repeating steps (g)-(h) until the consensus sequences no longer change.

The details of one or more embodiments are set forth in the accompanying drawings and the description below. Other features, objects, and advantages will be apparent from the description and drawings, and from the claims.

DETAILED DESCRIPTION

The most routinely typed HLA genes are HLA-A, HLA-B, HLA-C and HLA-DRB1. The gene structure of these alleles creates challenges which limit the usefulness of sequencing-based HLA typing. Specifically, for these alleles, exons 2 and 3 are each ~275 nt long and are separated from each other by a ~250 nt intron.

Without being bound by theory, it is widely held that the phase between these two exons can be important for donor-patient matching. Specifically, with reference to haplotyping, the phase of two exons refers to whether two particular alleles reside on the same chromosome or on separate chromosomes. Exons 2 and 3 combine to encode the peptide binding groove, a key functional domain of the HLA class I proteins expressed on the cell surface. Thus, knowing the phase between exons 2 and 3 allows an unambiguous determination of the proteins that are formed for an individual, and play an important role in donor-patient matching.

Typical sequencing-based haplotyping methodologies are ambiguous regarding phase. In typical HLA class I proteins, exons 2 and 3 are each approximately 275 nucleotides in length and are separated by an intron that is approximately 250 nucleotides in length. Many existing sequencing technologies do not exhibit read lengths that allow for complete sequencing of both exons as well as the intervening intron. Additionally, high error rates are associated with many sequencing technologies, and errors rates are typically increased as read length increases. The methods and systems presented herein overcome these deficiencies and provide a robust tool and cost-effective tool for determining HLA haplotype.

The methods and systems of the present disclosure provide for HLA haplotype determination even when read lengths are obtained that do not include complete sequences of two exons and an intervening intron. In particular embodiments, portions of a nucleic acid that are amplified, sequenced or otherwise used in a method herein can be non-overlapping. For example, a nucleic acid molecule that is amplified, sequenced or otherwise used in a method set forth herein can include (i) at least a portion of a first exon of an HLA gene; (ii) at least a portion of a second exon of the HLA gene; and (iii) an intron that is adjacent to the first and second exons, wherein a first portion of the intron is adjacent to the first exon and a second portion of the intron is adjacent to the second exon. The nucleic acid (or the above-described portions) can be optionally amplified and non-overlapping sequencing reads can be obtained. For example, a first sequencing read can be obtained that includes the first portion of the intron along with all or part of the first exon; a second sequencing read can be obtained that includes the second region of the intron along with all or part of the second exon, wherein the first portion of the intron and the second portion of the intron do not overlap. The HLA type of the individual from whom the nucleic acid was derived can be determined based on the non-overlapping sequencing reads.

Although the methods and systems presented herein are specifically described in the context of HLA typing, it will be understood by one of skill in the art that these methods have broad application to a variety of endeavors where sequence information is sorted into two or more sets. For example, in some embodiments, the methods and systems presented herein are useful for forensic applications, where short tandem repeats are sorted. In some embodiments, the methods and systems can be applied to sorting genomic variation in KIR region gene content. As another example, in some embodiments, the methods and systems can be applied to sorting RNA variability, including alternate splicing.

HLA Typing

Presented herein are methods and compositions for determining haplotypes in a sample. The methods are useful for obtaining sequence information regarding, for example, HLA type and haplotype. In some embodiments presented herein, the methods comprise selectively amplifying a nucleic acid molecule, and subsequently carrying out one or more sequencing reads of at least a portion of the amplified molecule. The identity of the amplified nucleic acid molecules is then determined based on the sequencing information.

Selectively Amplifying

In embodiments presented herein, a target nucleic acid is selectively amplified from a sample. In some embodiments, selectively amplifying can include one or more non-selective amplification steps. For example, an amplification process using random or degenerate primers can be followed by one or more cycles of amplification using target-specific primers.

As used herein, the terms "amplifying," "amplify," "amplification" and like terms refer to producing one or more copies of a single stranded or double stranded nucleic acid, or a portion thereof. In some embodiments, the methods provided herein can include a step of producing an amplified nucleic acid under isothermal or thermal variable conditions.

As used herein the term "selectively," when used in reference to "amplifying" (or grammatical equivalents), refers to preferentially amplifying a first nucleic acid in a sample compared to one or more other nucleic acids in the sample. The term can refer to producing one or more copies of the first nucleic acid and substantially no copies of the other nucleic acids. The term can also refer to producing a detectable amount of copies of the first nucleic acid and an undetectable (or insignificant) amount of copies of the other nucleic acids under a particular detection condition used.

Any suitable amplification methodology can be utilized to selectively or non-selectively amplify one or more nucleic acid molecules from an individual according to the methods and systems presented herein. It will be appreciated that any of the amplification methodologies described herein or generally known in the art can be utilized with target-specific primers to selectively amplify a nucleic acid molecule of interest. Suitable methods for selective amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to selectively amplify one or more nucleic acids of interest. For example, PCR, including multiplex PCR, SDA, TMA, NASBA and the like can be utilized to selectively amplify one or more nucleic acids of interest. In such embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to selectively amplify a target nucleic acid of interest. For example, in some embodiments, the selective amplification method can include ligation probe amplification or oligonucleotide ligation assay (OLA) reactions that contain primers directed specifically to the nucleic acid of interest. In some embodiments, the selective amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate assay (Illumina, Inc., San Diego, Calif.).

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455, 166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo$^-$ for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

A further approach that can be used to amplify gDNA in connection with the methods of the present disclosure is degenerate oligonucleotide primed polymerase chain reaction (DOP-PCR) under conditions such as, but not limited to, those described by Cheung et al., Proc. Natl. Acad. Sci. USA, 93:14676-79 (1996) or U.S. Pat. No. 5,043,272, the disclosures of which are incorporated herein by reference in their entireties. Low amounts of gDNA, for example, 15 pg of human gDNA, can be amplified to levels that are conveniently detected in the methods of the present disclosure. Reaction conditions used in the methods of Cheung et al. can be selected for production of an amplified representative population of genome fragments having near complete coverage of the human genome. Furthermore modified versions of DOP-PCR, such as those described by Kittler et al. in a protocol known as LL-DOP-PCR (Long products from Low DNA quantities-DOP-PCR) can be used to amplify gDNA in accordance with the present disclosure (Kittler et al., Anal. Biochem. 300:237-44 (2002), the disclosure of which is incorporated herein by reference in its entirety).

Primer-extension preamplification polymerase chain reaction (PEP-PCR) can also be used in a method of the present disclosure in order to amplify gDNA. Useful conditions for amplification of gDNA using PEP-PCR include, for example, those described in Casas et al., Biotechniques 20:219-25 (1996), incorporated herein by reference in its entirety.

In some embodiments, selective amplification can include a method to pull-down a nucleic acid of interest from a mixture of different nucleic acids. The pull-down can occur prior to or after amplification occurs. Pull-down methods are well known in the art, and can include, for example, nucleic acid pull-down using biotinylated probes or arrays of probes.

The present methods are not limited to any particular amplification technique and amplification techniques described herein are exemplary only with regards to methods and embodiments of the present disclosure.

In general, the haplotype sorting methods presented herein can be applied to any gene of interest. Specific embodiments described herein include haplotype sorting of HLA genes. In some embodiments, the HLA gene can be any HLA gene for which a haplotype is to be determined, including, for example, HLA genes HLA-A, HLA-B, HLA-C, DRB1, DQA1, DQB1, DPA1, and DPB1. In typical embodiments, the HLA gene can be, for example, HLA-A, HLA-B and HLA-C. The amplified nucleic acid can be, for example, the entire HLA gene, or any portion thereof. As described in greater detail below, the methods presented herein provide a sequencing-based solution to obtaining haplotype information regarding HLA genes such as HLA-A, HLA-B and HLA-C.

Figure 1:
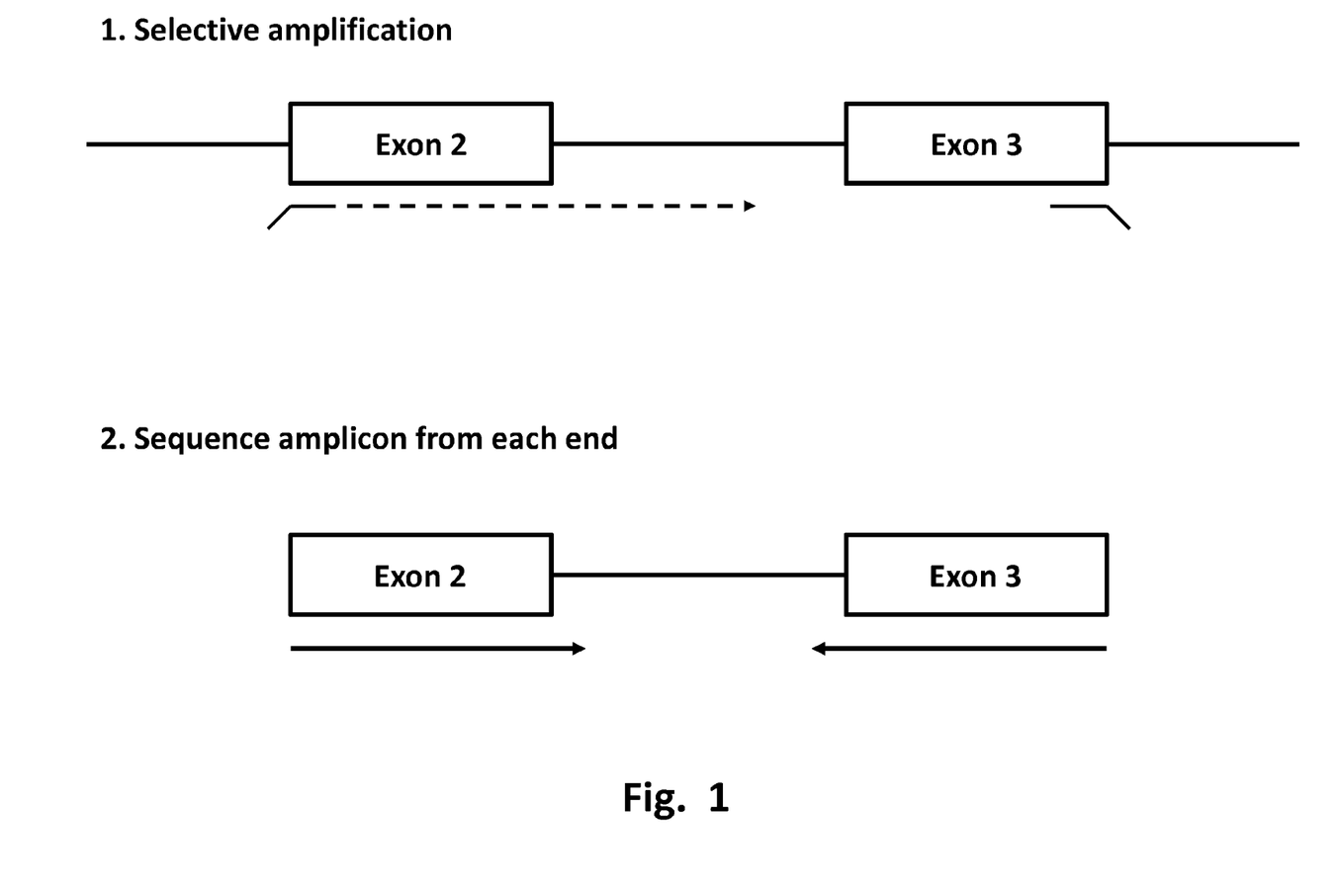
FIG. 1 is a schematic showing one embodiment of selective amplification of an exon pair followed by paired end sequencing of the exons, including the exon-intron boundaries.

In some embodiments, at least two exons of a gene such as HLA-A, HLA-B and HLA-C are selectively amplified. The two amplified exons collectively make up an amplified exon pair. In some typical embodiments, the two amplified exons are two adjacent exons of a gene such as HLA-A, HLA-B or HLA-C. In some typical embodiments, the two amplified exons are exons 2 and 3 of a gene such as HLA-A, HLA-B or HLA-C. In some embodiments, the amplified exons comprise the entire exon sequence of one or more exons. In some embodiments, the amplified exons comprise a portion of the exon sequence of one or more exons. The amplified exons in the amplified exon pair can reside on the same amplified nucleic acid molecule, as illustrated in FIG. 1. In some embodiments, the amplified exons in the amplified exon pair reside on separate nucleic acid molecules.

In some embodiments, the amplified exon pair comprises at least a portion of intronic sequence spanning between the two exons. In some embodiments, the amplified exon pair comprises the entire intronic sequence spanning between the two exons, as illustrated in FIG. 1. Without being bound by theory, it is widely held that the phase between these two exons is important for donor-patient matching. Thus, the methods presented herein provide a mechanism for obtaining exon phasing information. Specifically, the methods presented herein can include amplification of all or part of the intronic sequence between the exon pair followed by sequencing of the exon-intron boundaries.

The terms "target nucleic acid," "target nucleic acid molecule," "target nucleic acid species" and any grammatical equivalent thereof, refer to nucleic acid molecules that are desired to be amplified, sequenced or otherwise analyzed. Any of a variety of desired target nucleic acid molecules can be utilized, including but not limited to exons, or nucleic acid molecules complementary thereto; cDNA molecules, or nucleic acid molecules complementary thereto; untranslated regions (UTRs) or nucleic acids complementary thereto; promoter and/or enhancer regions, or nucleic acid molecules complementary thereto; evolutionary conserved regions (ECRs), or nucleic acid molecules complementary thereto; transcribed genomic regions, or nucleic acid molecules complementary thereto. Any of a variety of methods can be used to obtain targeted nucleic acid molecules, as disclosed herein. Such methods include, but are not limited to, obtaining a targeted nucleic acid molecule using hybridization-extension capture enrichment; using targeted restriction sites, for example, using an oligonucleotide engineered with a hairpin having a Type IIS restriction enzyme site such as a FokI restriction enzyme site and a locus-specific region; using locus-specific hyperbranched rolling circle amplification; using random-locus-specific primer amplification; using multiplex emulsion PCR; using multiplex bridge PCR; using padlock probe amplification; and using mini-libraries from targeted libraries, as disclosed herein.

As used herein, the terms "target nucleic acid sequence," "sample nucleic acid sequence" and like terms refer to nucleic acid sequences obtained from samples that are desired to be analyzed.

A nucleic acid sample that is amplified, sequenced or otherwise manipulated in a method disclosed herein can be, for example, DNA or RNA. Exemplary DNA species include, but are not limited to, genomic DNA (gDNA), mitochondrial DNA, chloroplast DNA, episomal DNA, viral DNA and copy DNA (cDNA). One non-limiting example of a subset of genomic DNA is one particular chromosome or one region of a particular chromosome. Exemplary RNA species include, without limitation, coding RNA such as messenger RNA (mRNA), and non-coding RNA (ncRNA) such as transfer RNA (tRNA), microRNA (miRNA), small nuclear RNA (snRNA) and ribosomal RNA (rRNA). Further species of DNA or RNA include fragments or portions of the species listed above or amplified products derived from these species, fragments thereof or portions thereof. The methods described herein are applicable to the above species encompassing all or part of the complement present in a cell. For example, using methods described herein the sequence of a substantially complete genome can be determined or the sequence of a substantially complete targeted nucleic acid sequences such as mRNA or cDNA complement of a cell can be determined.

Sequencing Read

In some embodiments presented herein, the methods comprise carrying out one or more sequencing reads of at least a portion of a nucleic acid such as an amplified nucleic acid molecule (e.g. an amplicon or copy of a template nucleic acid). The identity of nucleic acid molecules can be determined based on the sequencing information.

In sequence based typing of HLA genes, it can be important to obtain sequence information regarding an entire exon pair, including the exon-intron boundary. However, many sequencing technologies do not have read lengths that allow for complete sequencing of both exons as well as the intervening intron. The methods presented herein overcome an existing deficiency in existing HLA haplotyping technologies. In specific embodiments, amplified exon pairs are sequenced from both ends of the amplified molecule. In some embodiments, each sequencing read is of sufficient length to sequence the entire exon as well as at least a portion of the intervening intron. This technique of paired-end or pairwise sequencing is generally known and can be carried out, for example, as described in U.S. Pat. App. Publ. Nos. 2009/0093378, 2010/0311597, 2012/0053063, U.S. Pat. No. 8,192,930, U.S. Pat. No. 8,017,335 and U.S. Pat. No. 7,754,429, each of which is incorporated herein by reference.

Paired-end sequencing allows the determination of two reads of sequence from two places on a single polynucleotide template. One advantage of the paired-end approach is that although a sequencing read may not be long enough to sequence an entire target nucleic acid, significant information can be gained from sequencing two stretches from each end of a single template.

FIG. 1 illustrates one embodiment of this process. As shown in FIG. 1, an amplified exon pair is generated as described above. The primers used for amplification can comprise additional 5' sequence that can later be used in a subsequent sequencing read. For example, the additional 5' sequence can comprise sequence for hybridizing to a solid support, or for hybridization of a sequencing primer. In some embodiments, additional 5' sequence is added by ligating an adapter sequence. The embodiment shown in FIG. 1 shows sequencing reads that are initiated from both ends of the amplified product.

In some embodiments, each sequencing read is of sufficient length to sequence at least a portion of the amplified exon pair. In some embodiments, a sequencing read is long enough to sequence an entire exon of the amplified exon pair, or a portion thereof. In some embodiments, the sequencing read can include an exon-intron boundary. In some embodiments, each sequencing read is of sufficient length to sequence the entire amplified exon pair. Thus, in some embodiments, a sequencing read can be at least about 25, 50, 70, 100, 150, 200, 250, 300, 350, 400, 450, 500, 550, 600, 650, 700, 750, 800, 850, 900, 950 or 1000 or more nucleotides in length. For example, in some typical embodiments, a sequencing read of a first region can comprise at least 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or at least 500 nucleotides from the 5' end of the amplified exon pair. In some embodiments, a sequencing read of a second region can comprise at least 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or at least 500 nucleotides from the 3' end of the amplified exon pair. It will also be appreciated that sequencing of the one or more exons of an amplified exon pair can be primed from the intronic region, extending a sequence read towards and through either exon of the exon pair.

In some embodiments of the methods provided herein, one or more copies of the amplified nucleic acid molecule, such as an amplified exon pair, is sequenced a plurality of times. It can be advantageous to perform repeated sequencing of an amplified nucleic acid molecule in order to ensure a redundancy sufficient to overcome low accuracy base calls. Because sequencing error rates often become higher with longer read lengths, redundancy of sequencing any given nucleotide can enhance sequencing accuracy. Thus, in some embodiments, sequencing reads of the first and second regions of the amplified exon pair are performed multiple times. Thus, although the term "repeated" is used herein to refer to multiple sequencing reads of the same target nucleic acid molecule, the multiple reads need not be iterative. The multiple reads can be performed in parallel or they can be performed iteratively.

The number of sequencing reads of a nucleotide or nucleic acid is referred to as sequencing depth. In some embodiments, a sequencing read of at least the first region or second region of the amplified exon pair is performed to a depth of at least 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 900, 950 or at least 1000×. In typical embodiments, the accuracy in determining an HLA type increases proportionally with the number of reads. Example 2 below sets forth the surprising finding that 100% HLA typing accuracy can be achieved with sufficient sequencing depth.

The sequencing reads described herein may be performed using any suitable sequencing methodology, such as direct sequencing, including sequencing by synthesis, sequencing by hybridization, and the like.

One example is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. Flow cells provide a convenient format for housing amplified nucleic acid molecules produced by the methods of the present disclosure. One or more amplified nucleic acid molecules in such a format can be subjected to an SBS or other detection technique that involves repeated delivery of reagents in cycles. For example, to initiate a first SBS cycle, one or more labeled nucleotides, DNA polymerase, etc., can be flowed into/through a flow cell that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., *Nature* 456:53-59 (2008), WO 04/018497; U.S. Pat. No. 7,057,026; WO 91/06678; WO 07/123,744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. No. 6,210,891; U.S. Pat. No. 6,258,568 and U.S. Pat. No. 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. No. 7,595,883, and U.S. Pat. No. 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Exemplary methods for array-based expression and genotyping analysis that can be applied to detection according to the present disclosure are described in U.S. Pat. No. 7,582,420; 6,890,741; 6,913,884 or U.S. Pat. No. 6,355,431 or US Pat. Pub. Nos. 2005/0053980 A1; 2009/0186349 A1 or US 2005/0181440 A1, each of which is incorporated herein by reference.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents to one or more amplified nucleic acid molecules, the system comprising components such as pumps, valves, reservoirs, fluidic lines and the like. A particularly useful fluidic component is a flow cell. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666, which is incorporated herein by reference.

Haplotype Sorting

Also presented herein are methods of determining haplotypes in a sample based on a plurality sequence reads. Because sequencing data can be increasingly error-prone with longer read lengths, haplotype information may be difficult to sort out. The methods presented herein advantageously achieve accurate haplotype assignments by using redundant sequencing reads, thus overcoming the high error rates found in existing sequencing-based approaches. Additionally, data clustering methods presented herein also achieve efficient sorting of haplotypes from large sets of low-accuracy sequencing reads.

In some embodiments, the methods can comprise computer implemented steps of providing a computer readable memory comprising sequence information from a plurality of sequencing reads of a region of interest, the plurality of sequencing reads comprising sequence information from at least two different haplotypes; and partitioning each sequencing read into one of at least two different haplotypes, thereby determining haplotypes in the sample.

Any suitable method of partitioning can be utilized for the purpose of sorting a plurality of sequencing reads into two or more haplotypes. The partitioning methods presented herein surprisingly achieve effective sorting of haplotypes from large sets of low-accuracy sequencing reads. In certain embodiments, the partitioning method utilizes a data clustering approach. For example, in certain embodiments, a k-means clustering algorithm can be utilized. In certain embodiments, an expectation-maximization clustering algorithm is utilized.

In certain embodiments, partitioning comprises a k-means clustering algorithm. K-means is a partitioning clustering method based on K centroids of a random initial partition which is iteratively improved. In some embodiments, the clustering can comprise computer implemented steps of randomly selecting a first and second sequencing read from a computer readable memory and designating the reads as haplotype 1 and haplotype 2, respectively. Subsequently, each sequencing read in the plurality of sequencing reads is compared to haplotype 1 and haplotype 2 and assigned to either haplotype 1 or haplotype 2 based on sequence similarity to either haplotype 1 or haplotype 2. Using the sequence reads assigned to each haplotype, a consensus sequence is computed for haplotype 1 and for haplotype 2. In certain embodiments, the method further comprises designating the consensus sequences as haplotypes 1 and 2 and repeating the assignment and computing steps. This process (designating consensus sequences as haplotypes 1 and 2 and then assigning each read to one of the haplotypes, followed by computing new consensus sequences) can be repeated until the consensus sequences no longer change.

Figure 2:
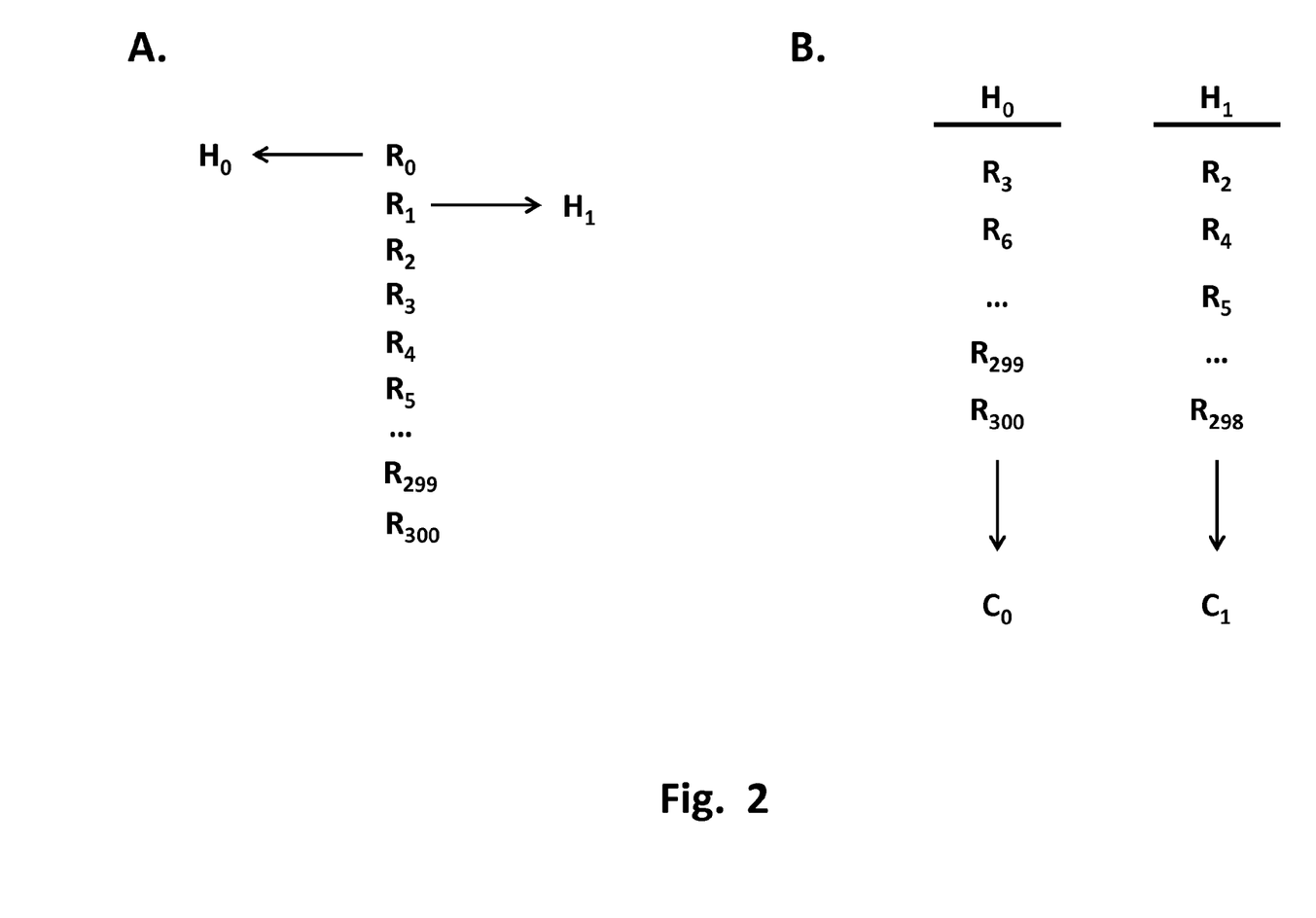
FIGS. 2A-C describe one embodiment of selective amplification of an exon pair followed by paired end sequencing of the exons, including the exon-intron boundaries.

This process is illustrated in FIG. 2. As shown in FIG. 2A, a plurality of sequencing reads is provided. In the particular embodiment illustrated in FIG. 2A, 300 sequencing reads ($R_0$ through $R_{300}$) are provided. Two of the reads (reads $R_D$ and $R_1$) are randomly selected and assigned as first and second haplotypes ($H_0$ and $H_1$). As set forth in FIG. 2B, the sequencing reads are then assigned to one of the two haplotypes for which it is most similar. Specifically, for each read, the number of mismatches with either $R_0$ or $R_1$ is calculated and the read is assigned to the haplotype with a minimal number of mismatches to that haplotype. After each read has been assigned to one of the two haplotypes, a consensus sequence ($C_0$ and $C_1$) is calculated for each haplotype. As shown in FIG. 2C, the process is then repeated again using consensus sequences $C_0$ and $C_1$ as the first and second haplotype sequences. The process can then be repeated, for example, until the consensus sequences $C_0$ and $C_1$ do not change.

In some embodiments, the methods can further comprise repeating the clustering method using a different pair of randomly selected initialization sequences. The clustering method can be repeated, for example, at least 2, 3, 4, 5, 6, 7, 8, 9, 10, 11, 12, 13, 14, 15, 16, 17, 18, 19 or at least 20 times. After the method has been repeated a desired number of times, the consensus sequences from each repeat can be compared to determine which pair of consensus sequences minimize the number of mismatches between the consensus sequence and the reads assigned to the haplotype assigned to the consensus sequence.

In other embodiments, partitioning is performed using an expectation maximization (EM) clustering algorithm. Unlike distance-based algorithms (such as K-Means), EM constructs statistical models of the underlying data source and naturally generalizes to cluster databases containing both discrete-valued and continuous-valued data. Thus, for example, in certain embodiments, each haplotype is modeled as a sequence of multinomial random variables. This approach has several advantages. First, haplotyping accuracy is improved over other clustering methods. Additionally, EM clustering provides probabilities for each consensus basecall in each of the two haplotypes. Such probability data can be useful, for example, when novel haplotypes are discovered.

Systems

A system capable of carrying out a method set forth herein can be, but need not be, integrated with a detection device. Rather, a stand-alone system or a system integrated with other devices is also possible. Fluidic components similar to those exemplified above in the context of an integrated system can be used in such embodiments.

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating a set of amplicons. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

Example 1

HLA-A Typing

This example describes a targeted PCR approach which, together with next generation sequencing, generates clinically relevant haplotypes for HLA-A, -B, and -C. Using a panel of 24 samples derived from two different populations, unambiguous haplotypes were obtained for three class I HLA genes, with an average fold-coverage of ~5200× per individual.

This approach for high resolution HLA typing incorporates next generation sequencing in which paired end read technology enables both ends of library template molecules to be read in a single MiSeq® (Illumina, San Diego, Calif.) run. Through a nested PCR approach, a set of sequencing primers were designed to be positioned immediately adjacent to exons 2-3 (class I) and exon 2 (class II) thereby enabling contiguous 2×300 bp sequence reads to be obtained. Due to the clonal nature of the library clusters, all reads were in phase, allowing unambiguous clinical haplotypes to be derived directly from the sequencing data.

Commercially available genomic DNAs for a set of 24 samples, consisting of CEPH (Utah residents with ancestry from northern and western Europe) (CEU) and Yoruba in Ibadan, Nigeria (YRI)) were purchased from the Coriell Institute for Medical Research. All of the CEU samples were previously typed (IMGT/HLA database), allowing for accuracy verification. For the YRI samples, trio-based phasing was used for accuracy testing. Approximately 10 ng of genomic DNA was used as the starting template for each assay. All samples were processed as follows: HLA targets were amplified with a set of outer PCR primers, yielding ~800-900 bp amplicons. These were diluted and served as template in a subsequent nested PCR reaction. The nested PCR served to enhance specificity of the final product and to position the sequencing primer directly adjacent to the exon-intron boundaries. Furthermore, sample barcodes were incorporated at this step for indexing each sample in the multiplex reaction. The final products were ~300-800 bp HLA-specific libraries, that were compatible with MiSeq® SBS chemistry.

Sequence reads that passed filter were first de-multiplexed and converted to FASTQ format. Reads were assigned to each individual based on their unique index reads. All correctly assigned reads were then further filtered to yield HLA-specific reads based on their respective PCR primer sequences. These filtered reads were then aligned locally to HLA-A, -B, and -C using the BWA aligner and the IMGT/HLA database.

A k-means-like clustering algorithm was applied, following the algorithm set forth below. Briefly, aligned/on-target reads were then clustered into groups such that reads within a cluster were similar to each other, while reads in different clusters were more dissimilar. Once clusters were identified the consensus sequence of the reads within each cluster was computed yielding haplotypes.

1. Sample two reads randomly and call them the two haplotypes
2. For each paired-end 300 nt read
   A. Compute the # of mismatches with haplotype 1
   B. Compute the # of mismatches with haplotype 2
   C. Assign the read to the haplotype for which it is most similar
3. Using the assignment of reads to the two haplotypes
   A. Compute the consensus sequence for haplotype 1
   B. Compute the consensus sequence for haplotype 2
4. Go back to Step 2, using the updated haplotypes (repeat until the haplotypes no longer change)

The procedure was repeated twenty times with different initializations. The run that minimizes the number of mismatches the reads have to their assigned haplotypes was selected as the final haplotype assignment.

This nested PCR approach, followed by paired-end 2×300 bp MiSeq SBS sequencing was able to generate HLA haplotypes for class I genes for two different populations (24 individuals). Example class I HLA haplotypes for two samples is shown in the table below. In the table below, the expected haplotype is the haplotype generated using Sanger sequencing. The observed haplotype is the haplotype called by the above-described procedure. The last two columns tell how many mismatches there are between the called sequence, and its closest match in the IMGT-HLA database.

| Sample | Locus | HAP1 Expected | HAP2 Expected | HAP1 Observed | HAP2 Observed | HAP1 Mismatches | HAP2 Mismatches |
|---|---|---|---|---|---|---|---|
| NA10831 | A | 01:01 | 01:01 | 01:01:01 | 01:01:01 | 0 | 0 |
| NA10831 | B | 08:01 | 51:01 | 08:01:01 | 51:01:01 | 0 | 0 |
| NA10831 | C | 07:01 | 15:02 | 07:01:01 | 15:02:01 | 0 | 0 |

-continued

| Sample | Locus | HAP1 Expected | HAP2 Expected | HAP1 Observed | HAP2 Observed | HAP1 Mismatches | HAP2 Mismatches |
|---|---|---|---|---|---|---|---|
| NA10835 | A | 02:01 | 23:01 | 02:01:01 | 23:01:01 | 0 | 0 |
| NA10835 | B | 40:01 | 41:01 | 40:01:01 | 41:01 | 0 | 0 |
| NA10835 | C | 03:04:01 | 17:01 | 03:04:01 | 17:01:01 | 0 | 0 |

The accuracy rates across the dataset ranged from ~90% (compared with the IMGT/HLA database) to ~94% (trio-inferred) accuracy. The average depth of coverage, across all three HLA genes was ~5200× per individual.

Example 2

Haplotyping HLA-A Gene Variants

Figure 3:
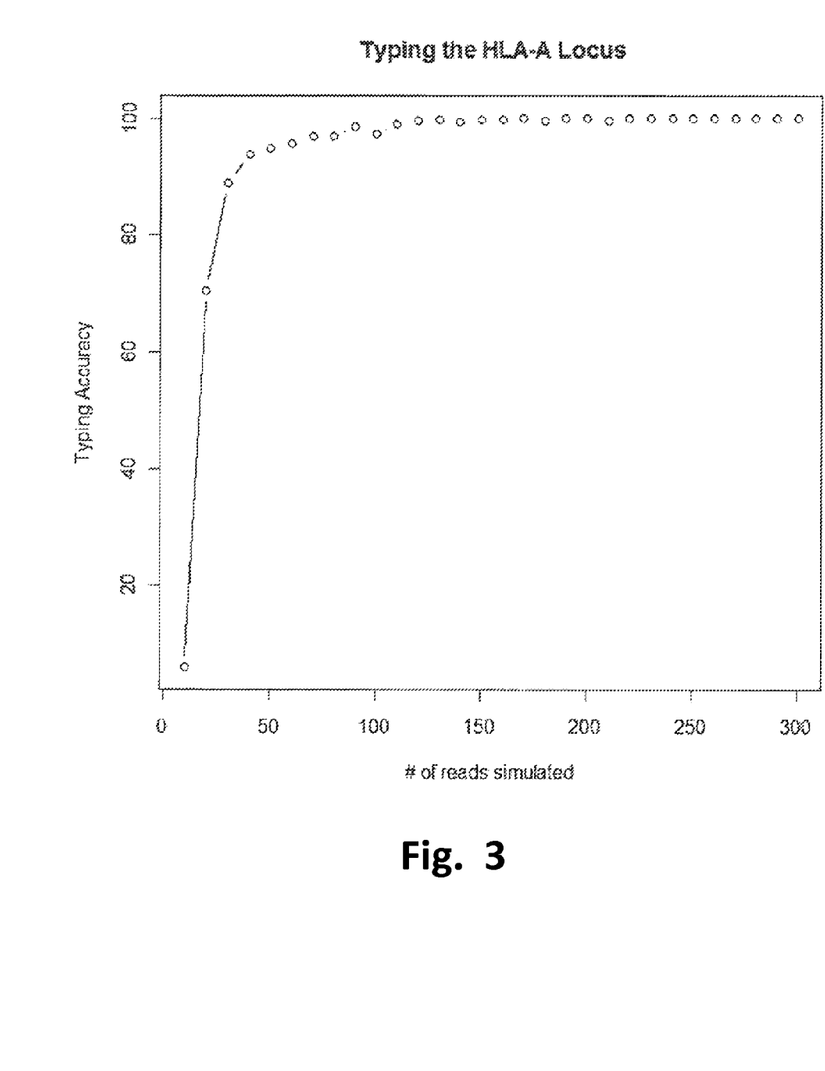
FIG. 3 is a graph showing haplotyping of the HLA-A locus, according to one embodiment.

Theoretical feasibility of the haplotyping method was tested via simulation. Random haplotype pairs for the HLA-A gene were sampled from the IMGT database of known HLA variants. Reads from these haplotypes were simulated with a realistic error distribution coming from empirical q-score strings from an Illumina MiSeq™ instrument. 1,000 haplotype pairs were generated and the number of simulated reads varied from 10, 20, . . . , 300. The ability to retrieve the simulated haplotypes was assessed. The results of the simulation are set forth in FIG. 3. As shown in FIG. 3, 100% typing accuracy was achieved with 300 sequencing reads.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of determining haplotypes in a sample comprising:
    (a) selectively amplifying a nucleic acid molecule from an individual, said nucleic acid molecule comprising
        (i) at least a portion of a first exon of an HLA gene;
        (ii) at least a portion of a second exon of said HLA gene; and
        (iii) the intron between said first and second exons, thereby generating an amplified exon pair;
    (b) carrying out a sequencing read of a first region of the amplified exon pair, said first region comprising at least a portion of said first exon and a portion of the intron adjacent to said first exon;
    (c) carrying out a sequencing read of a second region of the amplified exon pair, said second region comprising at least a portion of said second exon and a portion of the intron adjacent to said second exon;
    (d) performing steps (b) and (c) a plurality of times to generate a plurality of paired sequencing reads of said HLA gene, said plurality of paired sequencing reads comprising sequence information from at least two different haplotypes;
    (e) partitioning each sequencing read into one of two different haplotypes, wherein partitioning comprises computer implemented steps (f)-(i):
    (f) randomly selecting a first and second paired sequencing read and designating said reads as haplotype 1 and haplotype 2, respectively;
    (g) assigning each remaining paired sequencing read in said plurality of paired sequencing reads to said haplotype 1 or said haplotype 2 based on sequence similarity to either haplotype 1 or haplotype 2;
    (h) computing a consensus sequence for haplotype 1 and a consensus sequence for haplotype 2 using the paired sequence reads assigned to each haplotype; and
    (i) designating said consensus sequences as haplotypes 1 and 2 and repeating steps (g)-(h) until said consensus sequences no longer change;
    thereby determining haplotypes in said sample.

2. The method of claim 1, wherein said partitioning comprises application of a k-means clustering algorithm.

3. The method of claim 1, wherein said partitioning comprises application of an expectation-maximization clustering algorithm.

4. The method of claim 1, further comprising repeating steps (f)-(i) at least 2, 3, 4, 5, 6, 7, 8, 9, 10, 11, 12, 13, 14, 15, 16, 17, 18, 19 or at least 20 times and selecting the consensus sequences that minimize the number of mismatches between the consensus sequence and the reads assigned to the haplotype assigned to the consensus sequence.

5. The method of claim 1, wherein said assigning comprises computing the number of base mismatches between said sequencing read and the sequence of haplotypes 1 and 2.

6. The method of claim 1, wherein of said HLA gene is a Class I gene.

7. The method of claim 1, wherein of said HLA gene is a Class II gene.

8. The method of claim 1, wherein said HLA gene is selected from the group consisting of: HLA-A, HLA-B and HLA-C.

9. The method of claim 1, wherein said first region comprises at least 280, 290 or 300 nucleotides from the 5' end of said amplified exon pair.

10. The method of claim 1, wherein said second region comprises at least 280, 290 or 300 nucleotides from the 3' end of said amplified exon pair.

11. The method of claim 1, further comprising performing steps (b) and (c) a plurality of times.

12. The method of claim 1, wherein said selectively amplifying comprises an extension-ligation reaction.

13. The method of claim 1, wherein said selectively amplifying comprises a polymerase chain reaction.

14. The method of claim 1, wherein said sequencing reads are carried out in a sequencing-by-synthesis (SBS) reaction.

* * * * *